United States Patent [19]

Racette et al.

[11] 4,320,748
[45] Mar. 23, 1982

[54] FRACTURE BRACE

[75] Inventors: Walter L. Racette, La Habra; David L. Porter, Sunset Beach, both of Calif.

[73] Assignee: Orthomedics, Inc., Brea, Calif.

[21] Appl. No.: 208,504

[22] Filed: Nov. 20, 1980

[51] Int. Cl.³ .............................................. A61F 3/00
[52] U.S. Cl. ........................... 128/80 F; 128/DIG. 15
[58] Field of Search ................ 128/80 R, 80 F, 80 H, 128/83, 84 R, 87 R, 88, 89, 90 R, DIG. 15

[56] References Cited

U.S. PATENT DOCUMENTS

| | | | | |
|---|---|---|---|---|
| 1,336,695 | 4/1920 | Gromes | ............................... | 128/88 |
| 2,516,872 | 8/1950 | Hauser et al. | ..................... | 128/80 H |
| 3,064,644 | 11/1962 | Patterson | ......................... | 128/80 H |
| 4,050,455 | 9/1977 | Smith | ................................ | 128/80 F |
| 4,102,337 | 7/1978 | Golia | ................................ | 128/80 E |

*Primary Examiner*—John D. Yasko
*Attorney, Agent, or Firm*—Christie, Parker & Hale

[57] ABSTRACT

A fracture brace for a leg has an interior jacket for placement over the front of a leg, and for wrapping around the medial and lateral sides of a leg outside of a posterior shell. The posterior shell fits over the calf and the lateral and medial sides of the leg. Straps anchored on the shell unite the jacket and the shell to form an enveloping case for the leg that permits transmission of bearing pressures through the fleshy part of the leg, the tibia, and the brace. An interior pad integral with the jacket extends along the anterior of a leg from the proximal tibia to the distal tibia. There the pad wraps to the sides to provide padding for the bony prominences of the medial and lateral malleolus. A footplate connects to the jacket through a pair of uprights, each of which attaches to the footplate through a pivot and to the jacket by hook and pile fasteners. The attachment to the jacket permits adjustment of the footplate with respect to the jacket and therefore the foot with respect to the tibia: (1) in translation generally along the axis of the tibia, (2) in translation generally along an axis through the length of the foot, (3) in rotation generally around the axis of the tibia, and (4) in rotation generally about the axis through the length of the foot. The footplate can rotate about axes generally medial-to-lateral and through pivots connecting the footplate and the uprights.

17 Claims, 7 Drawing Figures

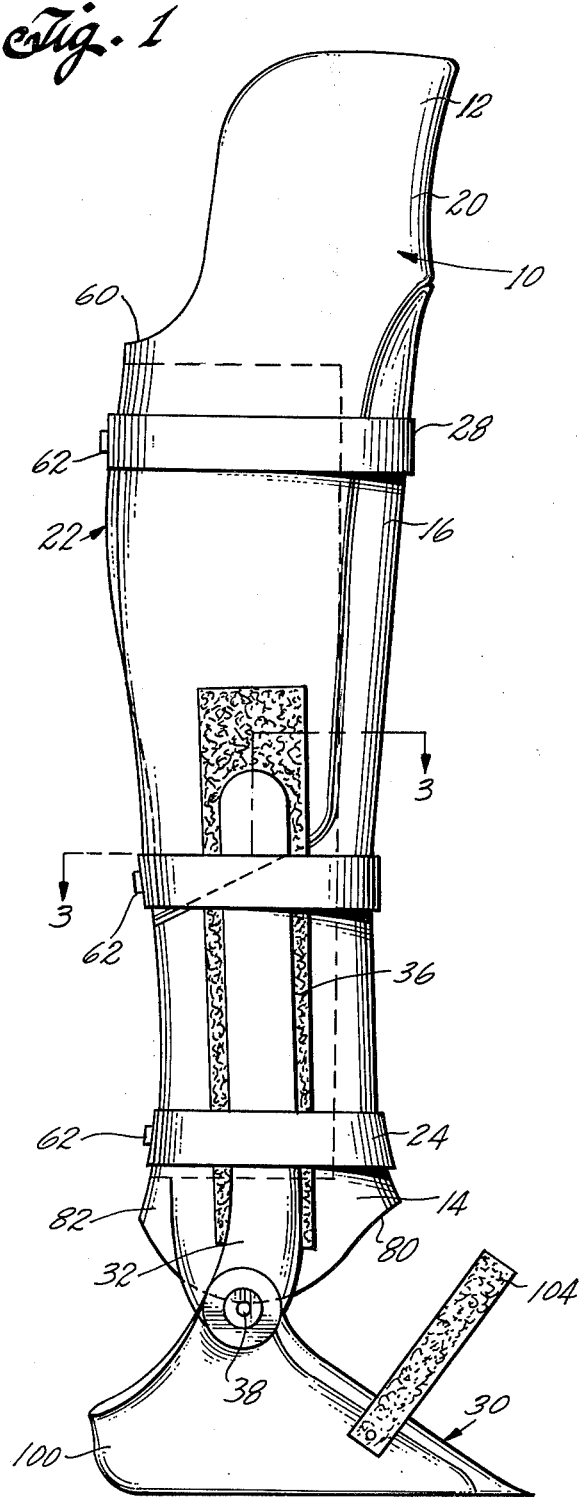

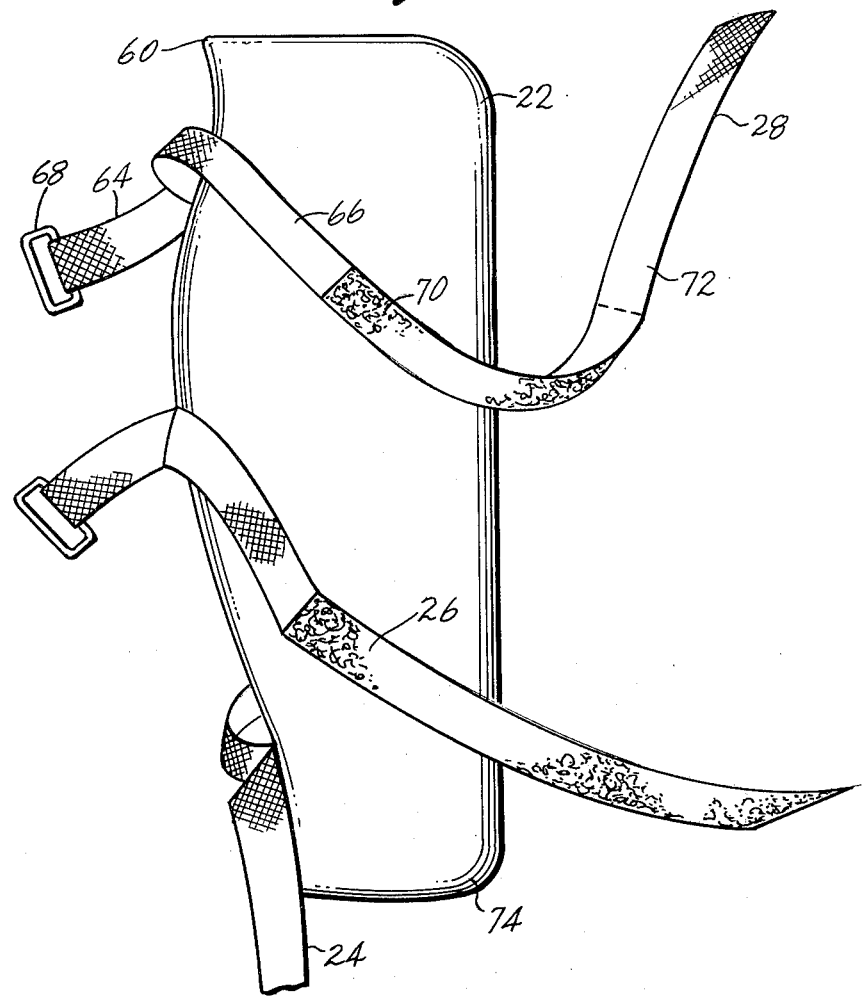
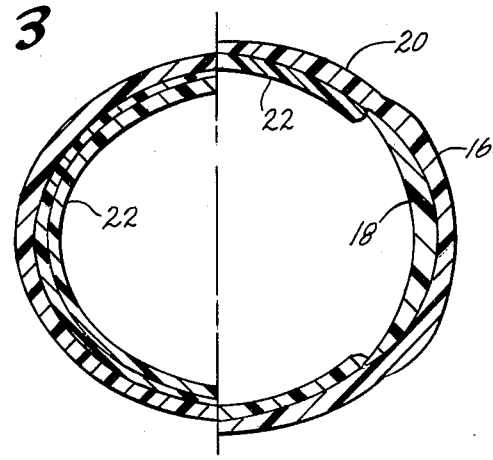

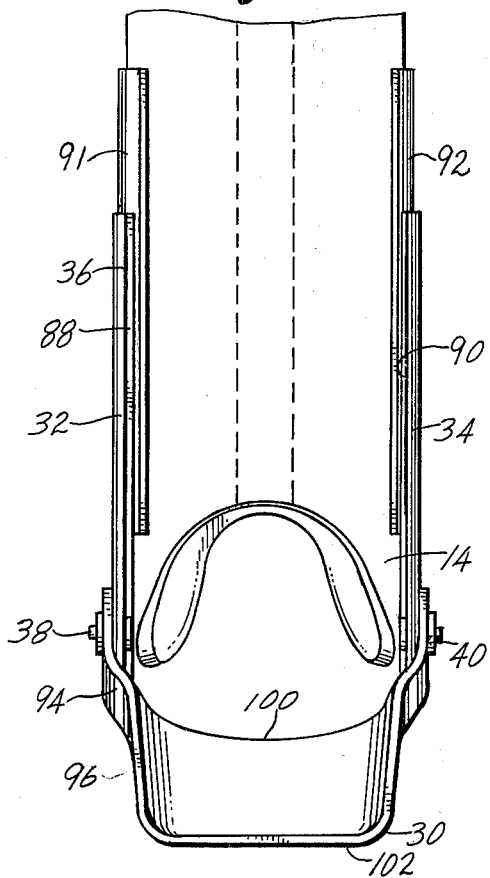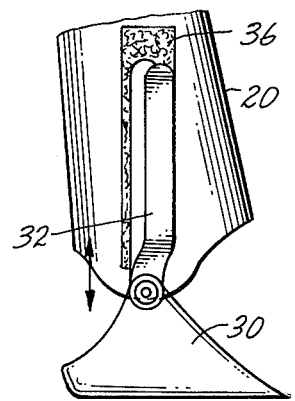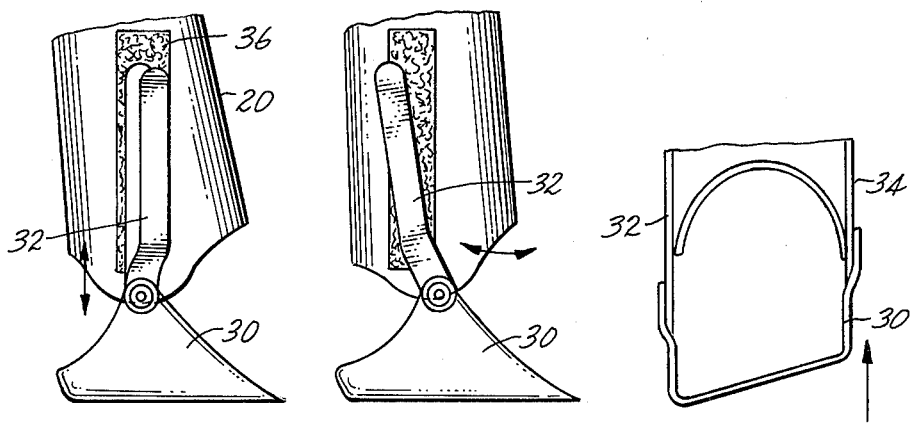

FRACTURE BRACE

BACKGROUND OF THE INVENTION

The present invention relates in general to fracture bracing and in particular to an improved fracture brace of the type that permits ambulation of a patient with a fractured tibia.

Traditionally, fractures of the tibia have been treated with a toe-to-groin cast of plaster of paris. The cast immobilized the ankle, leg, knee and thigh. The immobilization of the leg severely limits the mobility of the typical patient. A plaster cast is uncomfortable because of its weight and inability to relieve itching. Lack of ambulation can lead to joint stiffening and muscle atrophy.

Within the past few years it has been recognized that a special type of fracture brace or orthosis for tibia and fibula fractures can be used in place of toe-to-groin casts with efficacy after an initial period with the toe-to-groin cast. This fracture brace extends from the foot to the knee. It completely encases the involved leg in a rigid case. Loads from ambulation are transferred to the proximal part of the skeleton by the case, cased musculature, and the involved tibia and fibula. It has been found that this loading can enhance osteogenesis. Any shortening of the involved leg with this technique is of the same magnitude as with plaster casts. Any rotation and angulation of the involved bone is also of the same magnitude. The fracture orthosis permits proximal joint use and reduces atrophy. Incidence of non-union of the bones is less.

The acuteness of the initial injury usually results in appreciable swelling, discomfort, and soft tissue damage for which a toe-to-groin cast is necessary. A foot-to-knee fracture brace can be used after initial acute treatment in a toe-to-groin cast, or after soft tissue damage has healed. A use of the fracture brace with soft tissue damage can result in unacceptable discomfort because of pressure on the damaged tissue.

The foot-to-knee fracture brace has used footplates coupled to the brace with flexion joints to permit limited mobility of the ankle.

Some difficulties have been experienced in coupling the footplate to the fracture brace to accommodate required foot position with respect to the leg. Considerable constraint is required to avoid unacceptable angulation and rotation of an involved tibia and fibula. The proper position of the foot with respect to the leg is an absolute must to avoid trouble in these areas. The anatomies of different people compound the difficulty in designing suitable couplings between the footplate and the fracture brace.

Casts require removal to treat soft tissue damage, or to make adjustments necessary for the encapsulation required for the proper fit between the bone, cast, and soft tissue. Plaster-of-paris casts once removed cannot be reused, and are not adjustable. Orthoses using Orthoplast (a trademark of Johnson and Johnson) can be removed, adjusted, and reused, but with some difficulty.

Orthoses made of plastic have been employed in the past, but problems have been encountered in sizing such orthoses to accommodate the infinite sizes and shapes of the patients while at the same time providing effective encapsulation. Plastic, also, is hard and can irritate bony areas such as the bony prominences of the medial and lateral malleolus.

SUMMARY OF THE INVENTION

The present invention provides an improved, prefabricated fracture orthosis for fractures of the tibia, and permits patient ambulation and the benefits of stress at the fracture site.

The fracture orthosis includes an anterior jacket sized to wrap around the anterior of the leg and the lateral and medial sides of the leg. A posterior shell wraps around the calf and fits within the lateral and medial sides of the jacket. Straps at various places along the length of the orthosis tightly encapsulate a patient's leg within the shell and jacket and secure the shell and jacket to each other. A footplate attaches to the jacket at lateral and medial uprights, each attached to the footplate by a pivot. Fastener means between the uprights and the jacket rigidly secure the uprights to the jacket in any of an infinite number of positions to accommodate the requirements of a particular patient. These means permit adjustment in four degrees of freedom of the footplate with respect to the jacket: (1) elevation positioning of the footplate with respect to the jacket generally parallel to the axis of the tibia, (2) anterior-posterior positioning of the footplate with respect to the jacket, (3) rotation about axes corresponding in general to axes through the length of the foot, and (4) rotation about axes generally parallel to the axis of the tibia. Thus, for example, the elevational position of the medial upright can be elevated with respect to the elevational position of the lateral upright. This adjustment permits all necessary adjustment for angulation and rotation accommodation. The footplate, then, enjoys freedom of movement only about the axes of its pivots.

In preferred form, the present invention includes the anterior jacket and posterior shell being securable to each other through straps anchored at the middle of the posterior end of the shell to effect even loading on the calf. An anterior pad extends from the region of the patella to the region of the malleolus, and in the latter, completely sweeps around the orthosis. The pad narrows from the malleolus region to present the pad only along the shin. The uprights are made of fairly rigid plastic, but can accommodate some twist. They preferably attach to the jacket through hook and pile fasteners. These fasteners give the infinite degree of the adjustment between the footplate and the jacket. The jacket is capped by a patella shield that steps down behind the knee to accommodate knee flexion. A brim extends around the top of the jacket in the form of an outward flare. Hook and pile fasteners may be used on the straps of the shell in connection with a standard D-ring so that each strap can cinch up on itself by wrapping through the D-ring and fastening with the hook and pile fasteners. The interior pad flares at its interior margins into the balance of the jacket so as to present no ridges.

These and other features, aspects and advantages of the present invention will become more apparent from the following description, appended claims and drawings.

DESCRIPTION OF THE FIGURES

FIG. 1 is a side elevation of a right fracture orthosis of the preferred embodiment of the present invention;

FIG. 2 is a side elevation of a posterior shell of the fracture orthosis of FIG. 1;

FIG. 3 is a view taken in planes 3—3 of FIG. 1 showing in section a hard plastic outside of the anterior jacket and the soft interior liner;

FIG. 4 is a front elevational view of the fracture orthosis of the present invention with the top part of the jacket not being shown; and FIGS. 5 through 7 depict ranges of adjustment between the footplate and the jacket available with the orthosis of the present invention.

DESCRIPTION OF THE PREFERRED EMBODIMENT

FIG. 1 shows an improved orthosis for the leg in accordance with the present invention. It includes an anterior jacket 10 that extends from a patella shield 12 through an ankle shield 14. The interior of the jacket is partially lined with a soft plastic pad within the compass of a slightly raised case 16. FIG. 3 shows this soft lining at 18. The outside of the shell is formed of a hard, resilient material, such as polyethylene, and is indicated in FIGS. 1 and 3 at 20.

A posterior shell 22 is adapted to fit partially inside jacket 10 and is secured to the jacket by straps 24, 26, and 28 which are regularly placed along the length of the orthosis brace.

A footplate 30 connects to the jacket through lateral and medial uprights 32 and 34 (the latter shown in FIG. 4), respectively, and attachment means shown for upright 32 at 36. These means preferably include thistle cloth or hook and pile fasteners sold under the trademark "Velcro." The lateral and medial uprights are also preferably of plastic and are somewhat stiff, though each being capable of yielding slightly in torsion and bending with respect to its longitudinal axis.

Each upright attaches to footplate 30 through a pivot. For lateral upright 32, the attachment is through pivot 38. In FIG. 4, a pivot 40 provides the attachment for medial upright 34 to the footplate.

The jacket and the shell have a configuration generally conforming to the anatomical configuration of a leg. Their resilience permits shape changes to effect pressure contact with the soft tissue of a leg within a broad range of calf and ankle sizes. These two pieces of the orthosis tend to clamp in on the medial and lateral sides of a leg. Anterior-to-posterior adjustment for different leg sizes results from the shell moving in that direction with respect to the anterior jacket. In FIG. 1, such accommodation can be by relatively greater movement of the proximal or distal ends of the shell with respect to the jacket. For example, for a patient having a large calf and a small ankle the distal end of the shell can be moved further in the posterior direction than the proximate end of the shell.

Thus the orthosis provides for total encapsulation of a leg. This encapsulation permits the use of this particular type of fracture brace.

Briefly, it is known that ambulatory fracture bracing permits the application of acceptable loads on fractured tibias and fibulas as long as the soft tissue is totally encased. Some of the load passes to the proximal tibia past the fracture site through the hydraulic effect of the soft tissue of the leg. A small, but clinically effective amount of the load is borne by the tibia and fibula. Some of the load is borne by the brace.

The fact that the tibia and fibula bear some of the load enhances osteogenesis.

The orthosis can permit only very limited freedom of the footplate with respect to the jacket, except around the axes of the pivots of the footplate. The pivots should be proximate the anatomical ankle pivot. For proper angulation and rotation of the tibia, the degree of freedom of the foot with respect to the leg must be severely limited against motion in these directions. Yet different patients and fractures require different orientations of the footplate with respect to the jacket.

The present invention permits within outside limits an infinite number of orientations of the footplate with respect to the jacket in four degrees of freedom. A footplate attaches to the jacket through uprights and hook and pile fasteners. Each of the uprights can be translated longitudinally along the jacket, along the axis of the tibia, somewhat independently of the other. Thus, as seen in FIG. 7, upright 34 has been raised considerably with respect to upright 32 (FIG. 7 exaggerates the normal displacement). The relative movement results in rotation of the footplate about axes through the foot. This is a first degree of freedom. Each upright can be moved with respect to the jacket in an anterior-to-posterior plane to effect slight rotation of the footplate with respect to the jacket about longitudinal axes of the jacket generally parallel to a tibia. Such a displacement is shown exaggerated in FIG. 6, with upright 32 being rotated off the vertical around axes extending from the lateral to the medial. The curved arrows in FIG. 6 denote rotation about such an axis vertical with respect to the paper. This is a second degree of freedom. By moving the uprights together and vertically parallel to the axis of the tibia, a third degree of freedom is possible. FIG. 5 illustrates this, that the uprights can be moved vertically together with respect to the jacket. The phantom lines show one position for an upright and the solid line a second position. By moving the uprights in translation in anterior-to-posterior planes without rotation, a fourth degree of freedom is enjoyed. FIG. 6 shows compound movement, the two degrees of translation and one degree of rotation.

Jacket 10 is three-sided. It has an interior portion that confronts the shin and patella. It has a lateral portion for the outside of the leg that extends from the interior portion and curves inwardly as it progresses posteriorly in conformity with the shape of the lateral portion of the leg. A complementary medial portion of the jacket conforming in general to the medial side of the leg extends from anterior-to-posterior, curving inwardly. This curvature extends essentially completely from the ankle to the knee. Thus the jacket provides a substantial enclosing structure. The posterior of the jacket is open. The opening permits the jacket flexible bend about vertical axes into conformity with the shape of a leg. The flexibility permits accommodation to different perimeters along the length of a leg. It is substantially rigid against bending in the horizontal.

Space behind the jacket is closed by the posterior shell which itself wraps from the posterior end to the lateral and medial sides of a leg. The posterior shell is a general shape of a calf. It flares at its top to form a slight brim 60. The posterior shell extends from about the ankle to the top of the calf. It is flexible about vertical axes to conform to the shape of the calf, regardless of calf perimeter at different points along the length of the calf.

Straps 24, 26, and 28 secure to the posterior shell along its vertical medial centerline as by rivets 62. As can be seen in FIG. 2, each strap has a short and a long free end, for strap 28, a short end 64, and the long end 66. A D-ring 68 is secured at the very end of section 64.

A length of pile 70 and a length of hook 72 for a hook and pile fastener on section 66 enable the strap to secure to itself. By looping section 66 through D-ring 68 and doubling the section back onto itself, with the D-ring between the hook and pile sections, and securing the hook and pile sections together, the strap secures to itself and secures the posterior shell to the anterior jacket. An identical arrangement obtains for each of the other straps. Thus the gripping or securing length of the straps is infinitely adjustable within the limits of the hook and pile overlap. The shell can be made to rotate with respect to the jacket by changing the secured length of the straps.

The base of the shell flares slightly outwardly at 74 to prevent patient discomfort. If desired, the shell can have holes in it for breathing.

Jacket ankle shield 14 flares outwardly at 80 to match the curvature between the leg and the foot, also for patient comfort. A slight outward flare on the posterior side or end of the jacket, as is shown at 82, provides patient comfort.

Uprights 32 and 34 are rigid and semiflexible. As brought out earlier, the uprights are capable of some displacement in torsion or twisting about the longitudinal axis of the upright to accommodate adjustment of the footplate with respect to the jacket. Each upright is long relative to its width and thickness, and wide relative to its thickness.

FIG. 4 shows uprights attached to the footplate and the jacket as they appear in anterior view. Upright 32 has hook fasteners 88 along its interior side. Upright 34 has hook fasteners 90 along its interior side. A strip of pile 91 is secured to the jacket and cooperates with hook fasteners 88. A strip of pile 92 attached to the jacket cooperates with hook strip 90. Pivots 38 and 40, through which the upright is attached to the footplate, step laterally outward from the footplate to provide clearance between the patient and the pivots. For this purpose, and for pivot 38, a laterally displaced boss 94 steps outwardly from a vertical side wall 96 of the footplate. An identical arrangement exists for pivot 40. Footplate 30, in addition to vertical side wall 96, has a rounded posterior wall 100 and a base 102. As seen in FIG. 1, a strap 104 permits securing the foot within the footplate. The strap can join to itself through hook and pile fasteners.

The present invention has been described with reference to a preferred embodiment. The spirit and scope of the appended claims, however, should not necessarily be limited to the foregoing description.

What is claimed is:

1. An improved prefabricated fracture orthosis for a leg comprising:
   (a) an anterior jacket having an interior shape corresponding to the shape of a leg from about the ankle to the knee, an open posterior, and flexibility about vertical axes to contract and expand about a leg to conform to the leg;
   (b) a posterior shell for receipt in the jacket and having a closed posterior side, a shape generally conforming to the shape of a calf from about the ankle to the top of the calf, and flexibility about vertical axes to expand and contract into contact with the calf to conform to the calf;
   (c) means to secure the shell to the jacket while encasing a patient's leg to permit loading of the soft tissue of the leg and the tibia and fibula without unacceptable angulation or rotation;
   (d) a footplate;
   (e) a lateral and a medial upright each pivotally attached to the footplate to permit rotation of the footplate about generally horizontal, pivotal axes extending from the medial side of a patient's leg to the lateral side; and
   (f) means for attaching the medial and lateral uprights to the jacket with each upright having an infinite number of positions within predetermined ranges:
     (i) in vertical translation with respect to the jacket,
     (ii) in anterior-to-posterior translation with respect to the jacket,
     (iii) in rotation about axes generally normal to the longitudinal axis of the jacket and corresponding to the axis of a patient's foot, and
     (iv) in rotation about longitudinal axes of the jacket.

2. The orthosis claimed in claim 1 including padding in the inside of the jacket in the interior thereof corresponding to the areas of bony prominences of a leg and ankle.

3. The orthosis claimed in claim 2 wherein the padding is recessed within the jacket to present a continuous, uninterrupted surface between the padding and the jacket without a discontinuity in contact with a patient's leg.

4. The orthosis claimed in claim 3 wherein the jacket has an outwardly raised case receiving the padding.

5. The orthosis claimed in claim 3 wherein the padding extends circumferentially about the base of the jacket to encase the bony prominences of the malleolus and then extends in a comparatively narrow band along a zone corresponding to a patient's shin on the interior edge of the jacket to about the patella.

6. The orthosis claimed in claim 1 wherein the fastening means includes a plurality of straps secured along a medial vertical plane of the shell, each strap having fastening means permitting infinite adjustment of the securing length of the straps.

7. The orthosis claimed in claim 1 wherein the attachment means for the upright includes hook and pile fasteners, the hook and pile fasteners providing the infinite adjustment within the predetermined range.

8. The orthosis claimed in claim 7 wherein each of the uprights comprise a generally elongated member having a width in the anterior-to-posterior direction substantially greater than the thickness in the medial-to-lateral direction, and a vertical length substantially greater than both, each upright being generally flat and having limited flexibility to accommodate the position adjustment.

9. The orthosis claimed in claim 7 wherein the fastening means includes a plurality of straps secured along a medial vertical plane of the shell, each strap having fastening means permitting infinite adjustment of the securing length of the straps.

10. The orthosis claimed in claim 9 including padding in the inside of the jacket in the interior thereof corresponding to the areas of bony prominences of a leg and ankle.

11. The orthosis claimed in claim 10 wherein the padding extends circumferentially about the base of the jacket to encase the bony prominences of the malleolus and then extends in a comparatively narrow band along a zone corresponding to a patient's shin on the interior edge of the jacket to about the patella.

12. An improved prefabricated orthosis for a leg comprising:

(a) a jacket in the shape of a leg between the knee and the ankle and having an open back to provide flexibility to accommodate a range of perimeters of a patient's leg along its length, the accomodation within the range being infinite, whereby the jacket can contract to conform to the shape of a patient's leg;

(b) a posterior shell having the general shape of a patient's calf and enclosing the back of the jacket, the shell being flexible to accommodate different sized patient's legs by varying the perimeter and shaping the perimeter in an infinite number of positions along its length into correspondence with a patient's leg;

(c) means to attach the shell and the jacket while compressing a patient's leg between them, these attachment means being infinitely adjustable within a range;

(d) a footplate to support the bottom and sides of a patient's foot, the footplate having lateral and medial sides;

(e) a lateral and a medial upright pivotally attached to the lateral and medial sides of the footplate; and (f) hook and pile fasteners for attaching each of the uprights to the jacket and to provide within a range for each upright-to-jacket attachment infinite adjustment in four degrees of freedom:
  (i) in translation generally parallel to the longitudinal axis of the jacket,
  (ii) in translation in the anterior-to-posterior direction,
  (iii) in rotation about axes parallel to the longitudinal axis, and
  (iv) in rotation about axes generally normal to the longitudinal axis and along a patient's foot.

13. The orthosis claimed in claim 12 including padding means within the jacket for cushioning the orthosis against the bony prominences of a patient's leg, the padding means at the base of the jacket and in a zone corresponding to the bony prominences of the malleolus being coextensive with the perimeter of the jacket, the padding narrowing above this zone to present a comparatively narrow vertical strip extending to about the region of a patient's patella to cushion a patient's shin along the anterior side of the jacket.

14. The orthosis claimed in claim 13 wherein the padding and adjacent surfaces of the jacket define a continuous uninterrupted surface to avoid ridges that might irritate the patient.

15. The orthosis claimed in claim 14 wherein the jacket has an outwardly extending case receiving the padding.

16. The orthosis claimed in claim 15 wherein the jacket includes a patella shield having an outwardly flared brim at its top.

17. The orthosis claimed in claim 16 wherein the base of the jacket flairs outwardly to accommodate the turn between a patient's foot and leg.

* * * * *